(12) United States Patent
Arciniegas et al.

(10) Patent No.: US 8,262,889 B2
(45) Date of Patent: Sep. 11, 2012

(54) UNITARY ELECTRODE AND ELECTRODE SUPPORT FOR HORIZONTAL ELECTROPHORESIS

(75) Inventors: German Arciniegas, El Cerrito, CA (US); Eric Wallace, Napa, CA (US); Daniel Y. Chu, Hercules, CA (US); Jason McKee, Martinez, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 137 days.

(21) Appl. No.: 12/705,200

(22) Filed: Feb. 12, 2010

(65) Prior Publication Data

US 2010/0264030 A1    Oct. 21, 2010

Related U.S. Application Data

(60) Provisional application No. 61/154,269, filed on Feb. 20, 2009.

(51) Int. Cl.
*G01N 27/447* (2006.01)
*G01N 27/453* (2006.01)

(52) U.S. Cl. .................................. 204/616; 204/466
(58) Field of Classification Search .............. 204/600, 204/615–621, 466, 467
See application file for complete search history.

(56) References Cited

U.S. PATENT DOCUMENTS

| 4,608,146 A | 8/1986 | Penaluna |
| 4,693,804 A | 9/1987 | Serwer |
| 4,865,715 A | 9/1989 | Hellman |
| 6,451,193 B1 | 9/2002 | Fernwood et al. |
| 2003/0015426 A1* | 1/2003 | Rooney et al. ............ 204/467 |
| 2008/0217178 A1 | 9/2008 | Ben-Asouli et al. |

* cited by examiner

*Primary Examiner* — J. Christopher Ball
(74) *Attorney, Agent, or Firm* — Kilpatrick Townsend and Stockton LLP.; M. Henry Heines

(57) ABSTRACT

Horizontal electrophoresis is performed in a cell that includes a tank and a pair of electrodes, each mounted on an electrode support that is easily inserted into and removed from the tank, and once inserted, is secured in position by one or more spring-loaded, manual-release locking features.

18 Claims, 5 Drawing Sheets

UNITARY ELECTRODE AND ELECTRODE SUPPORT FOR HORIZONTAL ELECTROPHORESIS

CROSS-REFERENCES TO RELATED APPLICATIONS

This application claims the benefit of U.S. Provisional Patent Application No. 61/154,269, filed Feb. 20, 2009, the contents of which are incorporated herein by reference.

BACKGROUND OF THE INVENTION

1. Field of the Invention

This invention resides in the field of horizontal electrophoresis, i.e., electrophoresis performed in a horizontally oriented slab gel submerged in a liquid buffer solution.

2. Description of the Prior Art

Electrophoresis for the separation of proteins, nucleic acids, or other charged species in biological mixtures is performed in a variety of geometries and techniques. One of these is horizontal electrophoresis, in which the process is performed in a horizontally oriented slab gel submerged in a liquid buffer solution. This is also known as "submerged gel electrophoresis" or "submarine electrophoresis."

Submerged gel electrophoresis is commonly performed in specialized electrophoresis cells that are commercially available from various suppliers. While each cell has its own unique characteristics, the typical cell includes a tank that includes a raised platform to support the gel and a pair of elongated wells, one along each of two opposing edges of the platform, with an electrode in each well. As with all electrophoretic systems, leakage of the buffer solutions must be avoided, and the best cells are those that are readily disassembled for purposes of cleaning between runs and readily reassembled for repeated use. The present invention resides in a novel cell design that meets these needs.

SUMMARY OF THE INVENTION

Among the features of the present invention are a removable, unitary electrode support that extends into one of the electrode wells of the cell and supports both a wire electrode that extends into the well and an electrical plug that remains outside the well to connect the wire electrode to an external voltage source. In preferred embodiments, the electrode support is of unitary construction, which means that it is a single part, capable of being formed in a single forming step, such as molding, casting, or machining, and capable of insertion into the tank and removal from the tank as a single piece. The electrode support also contains a spring-loaded, manual-release connection or lock allowing the support and electrode to be manually inserted in a secure manner, and readily removed when needed, by simple finger pressure. An advantage of the spring-loaded manual release is that the support does not require a screw connection or any liquid-retaining features, such as an o-ring, to make the connection leak-free. Details of these and other features of the invention will be readily apparent from the description below and the Figures.

DETAILED DESCRIPTION OF THE INVENTION AND PREFERRED EMBODIMENTS

Figure 1:
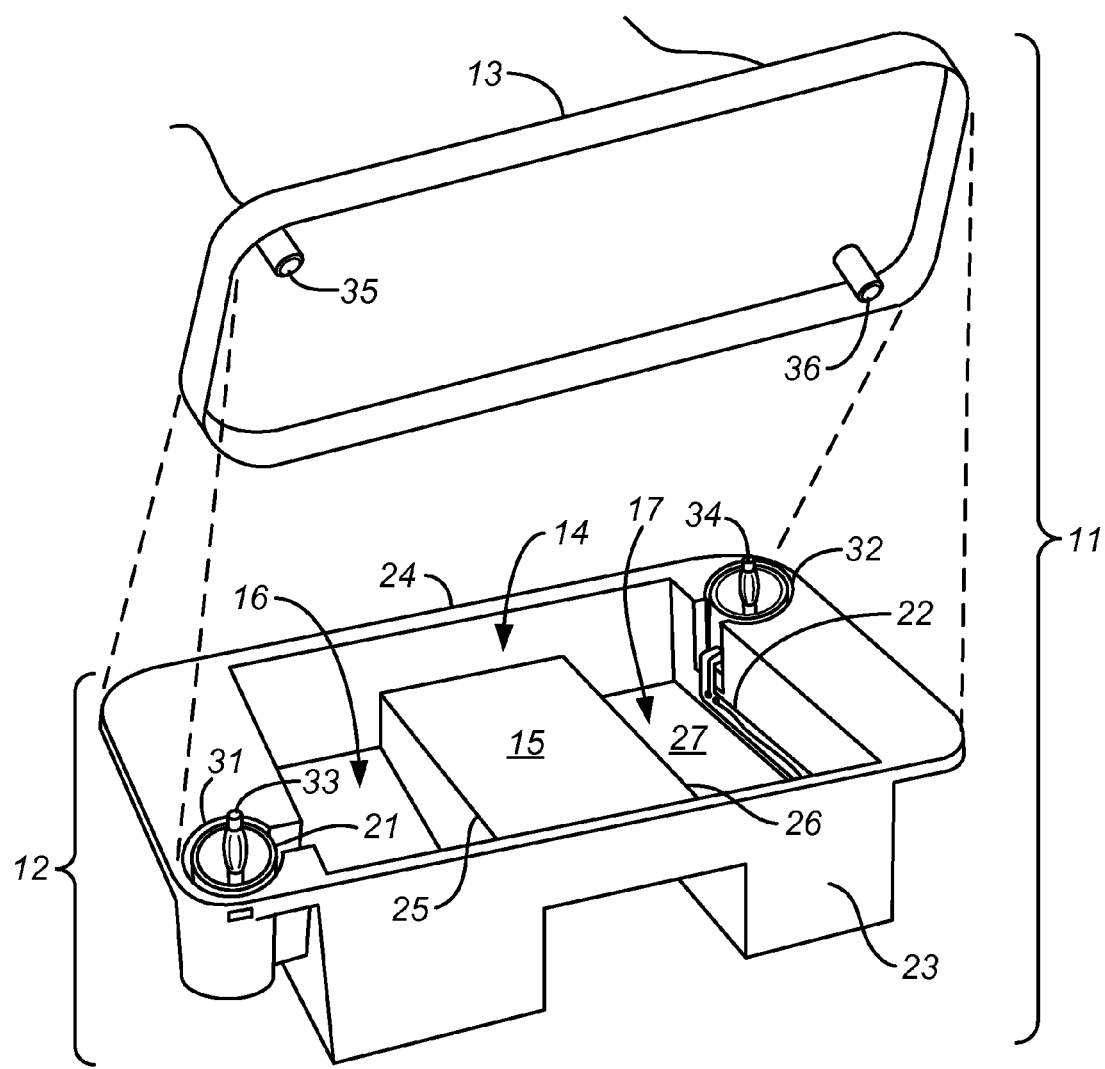
FIG. 1 is a perspective view of the a horizontal submerged gel electrophoresis cell in which the present invention can be implemented.

Each electrode support of the present invention is designed and constructed to hold a wire electrode in an extended configuration to span, at least substantially, the full length of one of the wells on either side of the raised platform that supports the gel. The support can thus be a bar, rod or strip, that fits within the well, with features thereon to hold the wire along the length of the support. Thus, when both supports are in place in their respective wells, a substantially uniform electric field is created along the length of the platform and the gel residing on the platform. Other than a bar, rod, or strip, the electrode support can assume the form of any frame across which the wire can be secured.

The electrical plug that forms part of the electrode support is affixed to a mounting member by which the electrode support is mounted to the tank. The mounting member is any fixture that will mate with or otherwise join a corresponding fixture on the tank to position the electrode in the well and to stabilize the electrode in that position. The mounting member can thus be a lug, a block, a tab, or any protrusion that projects from the bar that supports the wire electrode, and the mating fixture on the tank can be a recess, a slot, or any indentation or aperture that receives the mounting member. In preferred embodiments, the mounting member is a block with a hollow interior, with the electrical plug mounted in the hollow interior and accessible to external electrical connections. The block can be a square or rectangular block, or a circular block such as a cylinder, for example, and the mating fixture on the tank can thus be a square, rectangular, or cylindrical indentation or hollow in a side or end wall of the tank and slightly larger than the block to receive the block in a loose-fitting manner while holding the block in place. The indentation or hollow for securing each electrode support can conveniently be located in the end wall of the tank adjacent to the well in which the support is to be placed.

The electrical plug can be of any conventional design or configuration. Examples are banana plugs, clips, and jacks; other examples will be readily apparent to those skilled in electrical connectors. The electrical plug will be mounted to the electrode support in such a manner that the plug remains accessible and non-wetted when the tank is filled with buffer solution, so that the plug can be connected to an external power source without shorting. The exposed end of the plug thus preferably protrudes upward from the mounting member above the rim of the tank, while the opposite end resides within the interior of the mounting member where it is electrically connected to the wire electrode.

Electrode supports of unitary construction for use in the practice of this invention are those that can be inserted into the tank and removed from the tank intact, i.e., as a single unit. When the mounting member is a lug, block, or tab, the corresponding recess, slot, indentation, or aperture in the tank wall that receives the mounting member is preferably arranged such that the mounting member is inserted by simply lowering it into the recess, slot, etc., and removed by simply raising it, both without disturbing any liquids inside the tank. The recess, slot, etc., can thus have an open top to facilitate insertion and removal of the mounting member. The mounting member can be joined directly to the bar portion of the support, or through a web that connects the mounting member to the bar, particularly when the mounting member is a block. The web can thus be a narrow strip or bridge between the bar and the block, and can be inserted in a slot in the tank wall with the bar and block on opposite sides of the slot. Other variations and configurations will be readily apparent to those skilled in the art.

The spring-loaded, manually releasable lock for securing the mounting member to the tank can be of any configuration that holds the mounting member in position until released by the user. By "spring-loaded" is meant that the lock forms a resilient connection, either by use of an actual spring such as a foil spring, or a clip, or simply by the use of a strip or tab that can be bent to one side or otherwise distorted by the user's finger pressure and snaps back its original shape when the pressure is removed. The fixture is termed a "lock" to denote that the fixture is preferably designed to prevent disengagement of the mounting member by slipping out of the recess, slot, etc. in which the mounting member is inserted. The lock thus preferably secures the mounting member in place by more than a friction fit. This securement can be achieved by a protrusion on the spring-loaded part, such as a tab, knob, or hook, and a corresponding aperture or indentation in the wall of the recess.

The figures hereto and the following description represent examples of components that embody the features of the present invention.

FIG. 1 depicts an electrophoresis cell 11 in accordance with the present invention which includes a tank 12 and a lid 13 with the lid raised above the tank to show the internal features of the tank and features on the underside of the lid. The tank 12 is a molded plastic part with a central cavity 14 to hold buffer solution. Inside the cavity is a raised platform 15 to support a slab gel, the platform dividing the cavity into two wells 16, 17 with each well extending the length of one of two opposing edges of the platform 15. Electrode supports 21, 22 are placed inside the two wells 16, 17, each support having an exposed wire (only one of which is visible) extending substantially the full distance between the front wall 23 and the back wall 24 of the tank, parallel to the edges 25, 26 of the platform. The electrode supports place each wire at a height between the floor 27 of the well and the platform 15. When a slab gel is placed on the platform 14 and the tank is filled with buffer solution to a level above the platform 15, the gel will be submerged and a continuous electrical connection will be established through the buffer solution between the two electrodes and across the gel. Recesses 31, 32 in the end walls of the tank receive the mounting member sections of the electrode supports. Protruding upward from the electrode supports 21, 22 are electrical plugs 33, 34 that mate with jacks 35, 36 in the lid 13. Full electrical connections are this made by simply pressing the lid 13 down over the tank 12.

Figure 2:
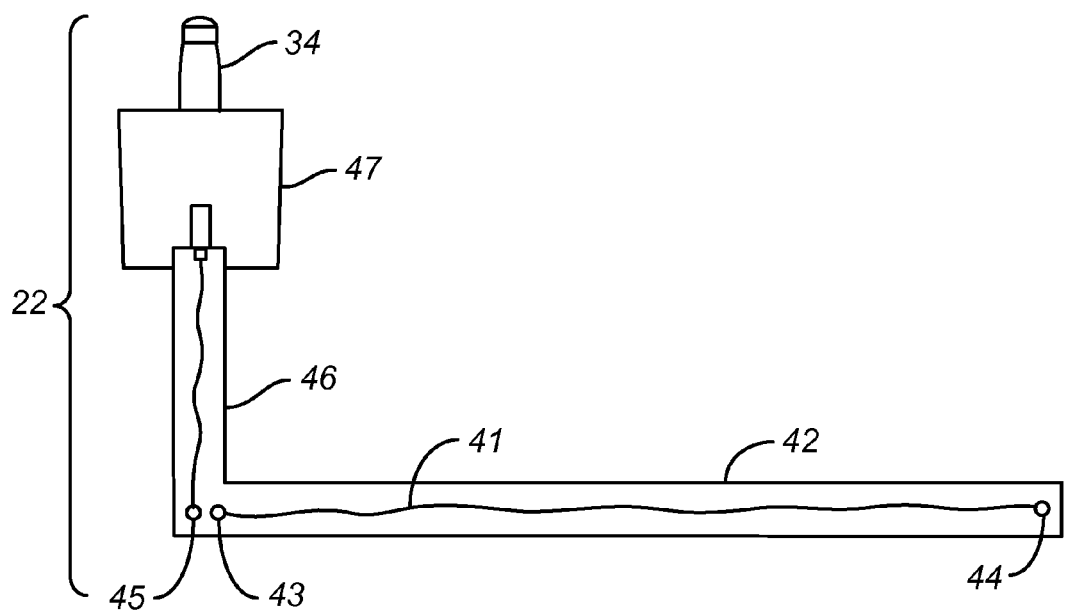
FIG. 2 is a front view of one of the two electrodes and its electrode support for the horizontal electrophoresis cell of FIG. 1.

FIG. 2 is a front view of an example of one of the electrode supports 21 with a wire electrode 41 secured to the support. The wire is stretched along the length of a straight bar 42 which is slightly shorter than the distance between the front wall 23 and the back wall 24 of the tank 12. When the electrode support is placed in the tank with the bar in a horizontal position inside one of the wells of the tank, the wire 41 is exposed on the side of the bar facing the platform inside the tank. Mounting of the wire to the bar is achieved in this embodiment by passing the wire through a pair of holes 43, 44 near the two ends, respectively, of the bar. The wire also passes through a third hole 45 from which the wire passes along a vertical connecting arm 46 and into the interior of the mounting member 47 where the bar is connected to the electrical plug 33. Segments of the wire other than the segment extending along the length of the bar 42 can be insulated by plastic tubing or other insulating material.

Figure 3:
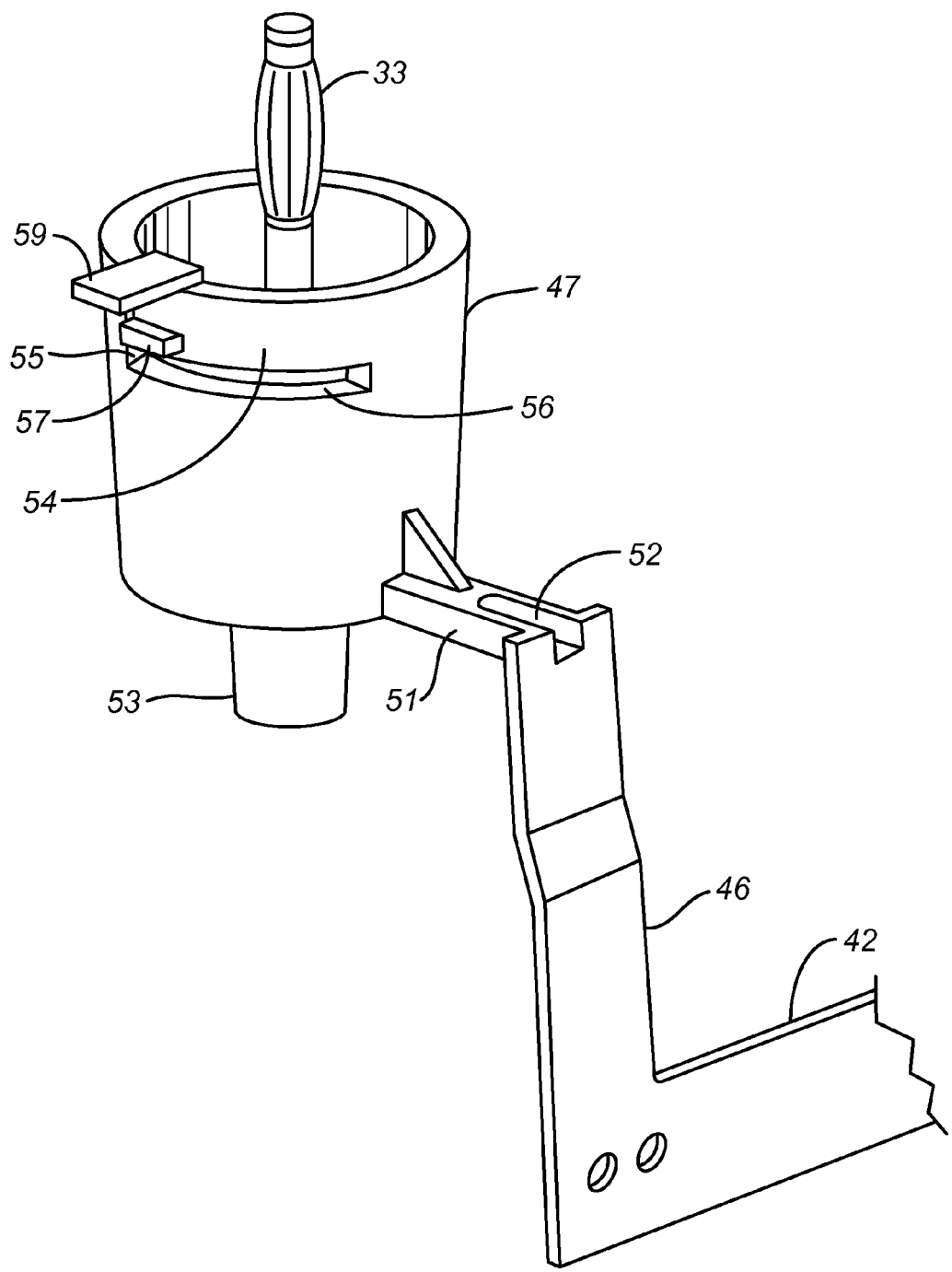
FIG. 3 is a perspective view of the mounting portion of the electrode support of FIG. 2.
Figure 4:
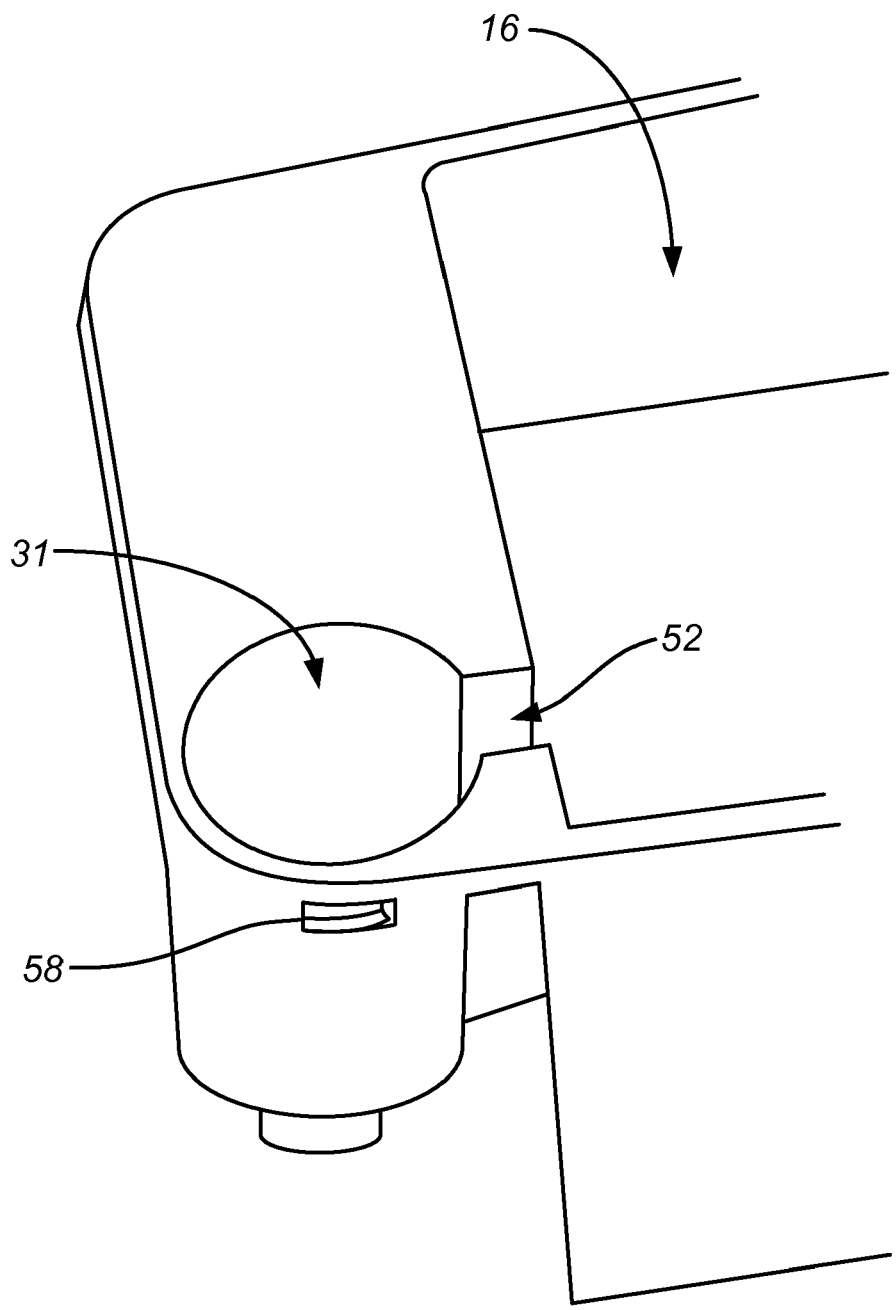
FIG. 4 is a perspective view of one end of the tank portion of the electrophoresis cell of FIG. 1.

FIG. 3 is a perspective view of the end of the electrode support that contains the mounting member 47. The mounting member 47 in this embodiment is a hollow cylinder that is closed at the bottom (not visible) and open at the top. The cylinder fits loosely inside, and is thus easily inserted into and removed from, one of the recesses 31 (FIG. 1, left side) in the tank end wall, which is also cylindrical in shape. An enlarged view of the tank end and the recess 31 is shown in FIG. 4. The mounting member 47 (FIG. 3) is joined to the connecting arm 46 through a bracket or web 51 that passes through a vertical slit 52 (FIG. 4) in the tank wall between the recess 31 and the adjacent well 15. The web 51 contains a groove 52 (FIG. 3) to serve as a guide for the wire. The groove 52 leads to an aperture (not visible) in the wall of the mounting member cylinder that opens into the interior of the hollow mounting member to join the electrical plug 33. The electrical plug 33 protrudes upward from the floor of the hollow mounting member 47 to be accessible for connection to the corresponding jack 35 in the lid (FIG. 1). A securing nut or boss 53 on the underside of the mounting member 47 (FIG. 3) secures the electrical plug 33 to the mounting member 47.

The spring-loaded, manual-release feature of the electrode support shown in FIG. 3 resides in a section 54 of the cylindrical wall of the mounting member formed by a vertical cut 55 and a horizontal cut 56 in the cylindrical wall. A tab 57 protruding from the section is aligned with a slot 58 (FIG. 4) in the wall of the recess 31 when the mounting member is inserted in the recess, thereby locking the mounting member in place. The section 54 serves as a resilient arm which can be pressed inward by the user to disengage the tab 57 from the slot 58 and will snap back to its original position when released. Manipulation of the resilient arm is made easier by a finger knob 59 on the upper rim of the mounting member.

Figure 5:
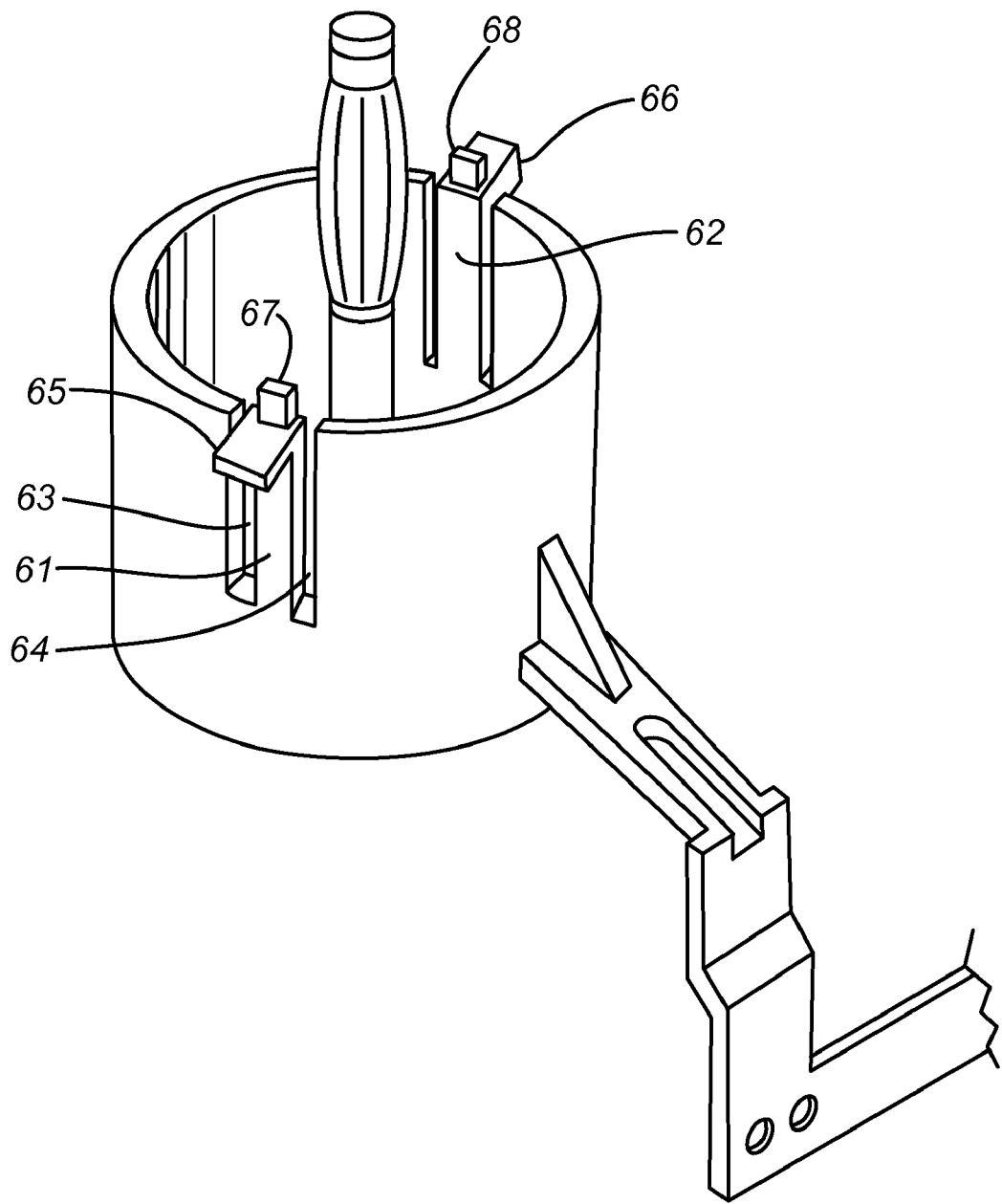
FIG. 5 is a perspective view of the mounting portion of an electrode support that is an alternative to that of FIG. 3.

An alternative design for the spring-loaded, manual-release feature is depicted in FIG. 5. The resilient aims 61, 62, of which two are shown in this example, are vertical (or axial relative to the cylindrical shape of the mounting member) rather than horizontal, and are formed by parallel vertical cuts 63, 64 rather than a short vertical cut and a longer horizontal cut as shown in the mounting member of FIG. 3. Each resilient arm of the mounting member of FIG. 5 has a tab 65, 66 extending outward from its side to mate with corresponding slots, apertures, or indentations in the wall of the recess, and a finger knob 67, 68 at its top for the convenience of the user.

In either design of the manual-release feature, the flexibility and resiliency of the arms are due to their lengths and shapes as well as the material of construction, which can be any of various plastic resins commonly used in the manufacture of electrophoresis cells and laboratory equipment in general. In either case, when a resilient arm is in its relaxed position, the tab on the arm protrudes into the corresponding slot in the wall of the recess, securing the entire electrode support in place in the tank. In use, an electrode support corresponding to either of those shown in FIGS. 3 and 4 will be placed on each of the two opposing end walls of the tank, oriented in opposite directions so that the two wire electrodes are both exposed toward the raised platform in the center. The section 54 of the embodiment of FIG. 3 is particularly useful when seeking to avoid contact of the electrical plug 33 with buffer solution from the adjacent electrode well.

Alternatives to the structures shown in the figures that are still within the concept of the present invention are shapes other than circular cylinders for the mounting member 47 and the recesses 31, 32. The mounting members and recesses can thus be polygonal (square, rectangular or polygons with three sides or five or more sides). Means of securing the bar 42 to the bottom of the tank or to the end wall of the tank, to stabilize the electrode and assure that the electrode is a fixed distance from the raised platform, can also be included. Features for this securement can include "keys" or "flags" as these terms are commonly used in the art. Furthermore, the number and placement of the resilient arm and tab features can vary. A single such arm and tab on each support can be used rather than two, or three or more per support can be used. Still further variations will be readily apparent to those skilled in the art.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A combination horizontal electrophoresis cell tank and removable electrode mounts, said combination comprising:
    a tank having a raised internal platform and a pair of elongated electrode wells, one such well on each of two opposing sides of said platform, each said well having a side wall with a recess therein, and
    a pair of electrode supports, each said electrode support comprising (i) an elongated bar having means thereon for supporting a wire electrode, and (ii) a mounting member projecting from said bar and insertable into one of said recesses such that when said mounting member is so inserted said bar resides in one of said wells, each said mounting member having an electrical plug mounted thereto and a spring-loaded, manually releasable lock for securing said mounting member in said recess.

2. The combination of claim 1 wherein each said recess has an open top above said platform and said recesses are shaped to permit insertion of said mounting members only by lowering said mounting members into said recesses through said open tops, and to permit removal of said mounting members only by raising said mounting members through said open tops.

3. The combination of claim 1 wherein each said electrode support further comprises a web joining said elongated bar to said mounting member, and said tank further comprises a slot between each said recess and adjacent well, said web fitting within said slot.

4. The combination of claim 1 wherein each said mounting member is a block with a hollow interior, and each said electrical plug is mounted within said hollow interior.

5. The combination of claim 1 wherein each said lock comprises a protrusion resiliently mounted to said mounting member, said combination further comprising an aperture or indentation in an internal surface of each said recess to receive said protrusion.

6. The combination of claim 1 wherein each said electrode support is of unitary construction, cast as a single part.

7. A horizontal electrophoresis cell comprising a combination cell tank and pair of removable electrodes in accordance with claim 1 and a lid with electrical contacts that mate with said electrical plugs when said tank with said electrode supports therein is closed with said lid.

8. A method for assembling a horizontal electrophoresis cell comprising a tank having a raised internal platform to support a gel flanked by a pair of elongated electrode wells, said method comprising:
    (a) placing a pair of wire electrodes mounted on electrode supports in said tank with one said wire electrode in each said well, each said electrode support comprising (i) an elongated bar to which said wire electrode is mounted and (ii) a mounting member projecting from said bar, by inserting each said mounting member into a recess in a side wall of said tank adjacent to each of said wells while securing said mounting members in said recesses by spring-loaded, manually releasable locks on said mounting members, each said mounting member having an electrical plug mounted thereto; and
    (b) connecting said electrical plugs to a power source.

9. The method of claim 8 wherein each said recess has an open top above said platform and step (a) comprises lowering said mounting members through said open tops.

10. The method of claim 8 wherein said mounting members are joined to said bars by webs and step (a) comprises inserting said webs into slots in said side walls between said recesses and said wells.

11. The method of claim 8 wherein each said mounting member is a block with a hollow interior, and each said electrical plug is mounted within said hollow interior.

12. The method of claim 8 wherein each said lock is a protrusion resiliently mounted to said mounting member, and said step of securing said mounting member in said recess comprises aligning said protrusion with an aperture or indentation in an internal surface of each said recess.

13. A method for electrophoretically separating species in a sample, said method comprising loading said sample onto a slab gel, and while said gel is on a raised internal platform in a tank that includes a pair of elongated electrode wells, one such well on each of two opposing sides of said platform, each said well having a side wall with a recess therein, applying a voltage between a pair of wire electrodes on electrode supports, each said electrode support comprising (i) an elongated bar having one of said wire electrodes mounted thereon, and (ii) a mounting member projecting from said bar and insertable into one of said recesses such that when said mounting member is so inserted said bar resides in one of said wells, each said mounting member having an electrical plug mounted thereto and a spring-loaded, manually releasable lock for securing said mounting member in said recess.

14. The method of claim 13 wherein each said recess has an open top above said platform and said recesses are shaped to permit insertion of said mounting members only by lowering said mounting members into said recesses through said open tops, and to permit removal of said mounting members only by raising said mounting members through said open tops.

15. The method of claim 13 wherein each said electrode support further comprises a web joining said elongated bar to said mounting member, and said tank further comprises a slot between each said recess and adjacent well, said web fitting within said slot.

16. The method of claim 13 wherein each said mounting member is a block with a hollow interior, and each said electrical plug is mounted within said hollow interior.

17. The method of claim 13 wherein each said lock comprises a protrusion resiliently mounted to said mounting member, said combination further comprising an aperture or indentation in an internal surface of each said recess to receive said protrusion.

18. The method of claim 13 wherein each said electrode support is of unitary construction, cast as a single part.

* * * * *